(12) United States Patent
Peschl

(10) Patent No.: US 12,201,957 B2
(45) Date of Patent: Jan. 21, 2025

(54) SPIRAL PHOTOREACTOR

(71) Applicant: Peschl Ultraviolet GmbH, Mainz (DE)

(72) Inventor: Alexander Peschl, Mainz (DE)

(73) Assignee: Peschl Ultraviolet GmbH, Mainz (DE)

( * ) Notice: Subject to any disclaimer, the term of this patent is extended or adjusted under 35 U.S.C. 154(b) by 0 days.

(21) Appl. No.: 18/713,670

(22) PCT Filed: May 15, 2023

(86) PCT No.: PCT/EP2023/062934
§ 371 (c)(1),
(2) Date: May 27, 2024

(87) PCT Pub. No.: WO2023/227403
PCT Pub. Date: Nov. 30, 2023

(65) Prior Publication Data
US 2024/0416316 A1    Dec. 19, 2024

(30) Foreign Application Priority Data
May 25, 2022   (EP) ..................... 22175518

(51) Int. Cl.
*B01J 19/12*     (2006.01)
*B01J 19/24*     (2006.01)

(52) U.S. Cl.
CPC .......... *B01J 19/122* (2013.01); *B01J 19/243* (2013.01); *B01J 2219/1203* (2013.01); *B01J 2219/1944* (2013.01)

(58) Field of Classification Search
CPC .................. B01J 19/122; B01J 19/243; B01J 2219/1203; B01J 2219/1944; B01J 19/087;
(Continued)

(56) References Cited

U.S. PATENT DOCUMENTS 6,932,903 B2 *   8/2005   Chang ..................... C02F 9/00
                                                      422/186.3
7,658,891 B1 *   2/2010   Barnes .................... C01B 13/11
                                                      128/205.28
(Continued)

FOREIGN PATENT DOCUMENTS

DE   102010014712        6/2011
DE   102014012218 A1     2/2016
EP   3881930 A1          9/2021

*Primary Examiner* — Xiuyu Tai
(74) *Attorney, Agent, or Firm* — Smartpat PLC

(57) ABSTRACT

A helical photoreactor includes a lamp module and a tube coil, which has a plurality of tube windings between an input section and an output section. The tube coil is arranged around the lamp module. The helical photoreactor has a carrier device, which carries the tube coil, and a protective housing, which surrounds a receiving space, in which the carrier device with the tube coil and the lamp module are arranged. The carrier device provides a predetermined positioning of the tube coil with respect to the lamp module and the protective housing. An elongated guide element, on which an engagement element is arranged so as to be capable of being guided in a longitudinally movable manner and so as to be capable of being positioned. The elongated guide element specifies the positioning of the carrier device with the tube coil by the engagement element guided on the elongated guide element.

10 Claims, 5 Drawing Sheets

(58) Field of Classification Search
CPC ...... B01J 19/123; B01J 19/127; B01J 19/128; B01J 2219/19; B01J 19/0013; B01J 19/2415; B01J 19/121; B01J 2219/192; B01J 2219/00096; B01J 2219/126; B01J 2219/0875; B01J 2219/0877; B01J 2219/0871; C02F 2201/3228; C02F 1/725; C02F 1/325; C02F 2201/3222; C02F 2301/026; C02F 2201/3227; C02F 2305/10; C02F 2201/222; C02F 2201/3223; C02F 1/30; C02F 1/32; H01L 21/67051; H01L 21/02057; H01L 21/67766; H01L 21/67742; B08B 7/0057; Y02W 10/37; C12M 21/02

See application file for complete search history.

(56) References Cited

U.S. PATENT DOCUMENTS

| | | |
|---|---|---|
| 8,067,749 B2 | 11/2011 | Kauling et al. |
| 8,890,087 B2 | 11/2014 | Ben-David et al. |
| 2020/0188968 A1* | 6/2020 | Choi ................ H01L 21/67766 |
| 2023/0135557 A1 | 5/2023 | Broersma et al. |

* cited by examiner

SPIRAL PHOTOREACTOR

CROSS-REFERENCE TO RELATED APPLICATION

This application is a national stage application, filed under 35 U.S.C. § 371, of International Patent Application PCT/EP2023/062934, filed on May 15, 2023, which claims the benefit of European Patent Application EP 22175518.4, filed on May 25, 2022.

TECHNICAL FIELD

The disclosure relates to a helical (or spiral) photoreactor for the continuous production of a photochemical reaction product.

BACKGROUND

It is known from the prior art that various factor influence the yield, which can be attained by means of the photochemical reaction, during the development of photoreactors. The simplest approach exists in the case of a batch reactor comprising one or several immersion lamps and a circulating means, such as a pump or an agitator, which ensure that the reaction medium provided in the reactor is moved turbulently. Even though a batch reactor allows for a process monitoring comparatively easily, the suitability for the large-scale production on an industrial scale is limited, however.

Photoreactors suitable for the continuous operation are tubular photoreactors, which, mostly constructed in the horizontal or vertical direction, are also used on a large scale. Tubular photoreactors often consist of at least two coaxial tubes, wherein a radiation source is located in the inner tube, and the reaction medium is guided through the annular gap between the outer and the inner tube along the radiation source.

The scaling of a photochemical reactor for the continuous operation from the laboratory to the pilot scale and in particular to the industrial scale is often associated with difficulties thereby and, due to a lack of adequate models for the transfer of photonic energy into chemical energy, is mostly carried out semi-empirically. This means that in response to the scaling of photochemical reactors from the laboratory scale into the production scale, changes have to mostly be made to the construction, which go beyond a pure enlargement because it is important to keep the ratio of irradiated volume to the reactor volume and the incident photon flux density constant. Influencing variables, which should be considered during the enlargement of the construction, relate, for example, to flow ratios in the reaction medium as well as to distances, phase limits and wall thicknesses, which can lead to the partial scattering and/or absorption of the used radiation.

A modular photo tubular reactor is thus proposed in DE 102010014712 B3, in order to provide for the scaling to production scale at optimized reaction control in a cost-efficient manner and with little expenditure of time. For this purpose, the photo tubular reactor, by means of which fluid media can be treated photochemically, has a centrally axially arranged irradiation unit. The latter includes at least one radiation source and is coaxially surrounded by a reactor wall, which is limited on one end by a head piece comprising fluid inlet and, on the other end, an end piece comprising fluid outlet. Depending on the length of the irradiation unit, the reactor wall consists of two or more cylindrical reactor segments, wherein adjacent reactor segments are connected by means of an intermediate flange, the inner diameter of which corresponds to the inner diameter of the reactor segments, so that the width of an annular gap between the irradiation unit and the reactor wall along the reactor length is constant.

From the field of photobioreactors, it is further known for the cultivation of phototropic organisms (e.g., algae, cyanobacteria), to use a modification of a tube reactor, which is referred to as hose, spiral or helical photoreactor, in particular at the laboratory or pilot scale. A flexible transparent hose is thereby wound helically around a light source, so that, with the same length of the light source, a longer dwell time of the reaction medium in the irradiated region can be attained than in the case of a coaxial tubular photoreactor.

However, photobioreactors can only be compared to chemical photoreactors to a limited extent because photobioreactors for an optimal growth of microorganisms are mostly operated with conditions, which correspond to sunlight, ambient pressure and room temperature. Photobioreactors thus mostly do not meet the requirements for the use in the photochemical field, in that the reaction conditions can often deviate very significantly from the room temperature and ambient pressure. During the construction of photochemical reactors of any magnitude, the safety requirements are to further be considered, which can develop due to the use of ignition sources, such as the radiation sources and the corresponding electronics, when the reaction medium used during the photochemical reaction contains flammable or ignitable materials, respectively.

A helical photoreactor comprising a lamp module, which surrounds a reactor housing, in which a wound duct is formed, is known from U.S. Pat. No. 8,067,749 B2. A transparent carrier tube carries the reactor housing, and a protective housing surrounds a receiving space, in which the carrier tube with the reactor housing and the lamp module are arranged.

EP 3 881 930 A1 likewise discloses a helical photoreactor comprising a tube coil, which is arranged around the lamp module. Windings are formed in the tube coil between an input section and an output section, wherein the tube coil is carried by a carrier device. A protective housing surrounds a receiving space, in which the carrier device with the tube coil and the lamp module are arranged.

SUMMARY

According to a first embodiment, an improved the helical photoreactor is formed for the continuous production of a photochemical reaction product. The helical photoreactor has at least one lamp module and at least one tube coil. The tube coil has a plurality of tube windings between an input section and an output section. A reactant fluid supplied on the input section passes through the tube windings as reaction medium, which is discharged on the output section as product fluid, which contains the photochemical reaction product or consists thereof. The at least one tube coil is arranged with the tube windings around the at least one lamp module, wherein at least the tube windings of the tube coil are transparent for an operating radiation of the lamp module. In the present case, "operating radiation" is understood to be electromagnetic radiation of a certain wavelength or certain wavelengths or wavelength ranges, respectively, which are suitable for performing the photochemical reaction for the production of the respective photochemical reaction product. The operating radiation for photochemical reactions thereby often lies in the UV range, but can, in contrast, generally also lie in the visible spectral range.

"Transparent for the operating radiation" thereby means that the tube windings consist of a material and have a wall thickness, which provide a transmission degree of at least 75% for the operating radiation. The helical photoreactor thereby has a carrier device, which releasably carries the at least one tube coil. A protective housing of the helical photoreactor surrounds a receiving space, in which the carrier device with the at least one tube coil and the at least one lamp module are releasably arranged. The carrier device is formed to provide a predetermined positioning of the tube coil with respect to the at least one lamp module in the protective housing. At least one elongated guide element lies, for this purpose, in the protective housing parallel to a longitudinal axis, which is defined by the lamp module or by the tube coil, respectively. The carrier device has at least one engagement element, which can be guided on the elongated guide element in the longitudinal direction and which can be arranged in a position, which is predetermined for the tube coil. The elongated guide element thus specifies the positioning of the carrier device with the tube coil by means of the engagement element guided on the elongated guide element.

Due to the fact that the reaction conditions of photochemical reactions often demand higher pressures and are associated with increased temperatures and the reaction medium can optionally contain hazardous substances, the protective housing serves the purpose of protecting the surrounding area from contaminations or injuries, respectively, caused by leakages on the tube coil or the connections thereof. The protective housing is thus embodied in a correspondingly pressure-tight manner. The protective housing can further serve the purpose of shielding the radiation of the lamp module to the outside, in that the protective housing is made of a material, which is not transparent for the operating radiation and which is additionally preferably inert or at least sufficiently stable with respect to the operating radiation and the chemicals used in the helical photoreactor.

The carrier device advantageously provides for a simple assembly and disassembly of the tube coil in the protective housing separately from the assembly or disassembly of the lamp module, respectively. Installation and replacement of the tube coil for the maintenance or adaptation are significantly simplified thereby. The maintenance replacement of a tube coil can become necessary when, for instance, the material of the tube coil becomes brittle as a result of the operating radiation or intransparent, e.g., due to deposits or debris.

As transparent hose, for example, the tube coil can consist of a flexible (plastic) material. The transparent hose can be formed into the tube coil with the desired windings with the help of the carrier device. Alternatively, the tube coil can consist of a transparent rigid glass or plastic material with firmly formed windings, which are held by the carrier device. In both cases, the windings of the tube coil can follow a curve, which winds around the jacket of an imaginary circular cylinder, preferably with constant pitch. However, the windings of the tube coil can also deviate from an even screw course, in order to vary, for instance, the impinging radiation quantity/density along the course of the tube coil. It is therefore also conceivable that the windings of the tube coil wind with varying pitch and/or around the jacket of an imaginary truncated cone or of another rotational body or of a body with polygonal base surface, respectively, such as, for example, of a prism or of a pyramid. Deviating from a common screw course with consistent direction of rotation, the windings can further have changes of the direction of rotation along their course and can be guided, for example, in a meander-shaped manner, along the central axis from the top to the bottom and around the central axis. A tube coil is to generally be understood to be any tube structure, the course of which extends along and around the jacket of an imaginary geometric body, which can be a cylinder, a prism, a truncated cone or truncated pyramid or can consist of two or more of those mentioned, so that the tube structure surrounds the lamp module at least in the radiation region thereof.

For the simple adaptation of the tube coil to different lamp modules for changing the throughput or the photochemical reaction and to optimize the yield of the reaction product, the carrier device makes it possible to receive different tube coils. They cannot only differ with respect to material, but also with respect to tube diameter and wall thickness and pitch of the coil. The carrier device can optionally also be formed to receive tube coils, which have different coil diameters, in order to be able to vary the distance of the windings from the lamp module. The number of the windings, which a tube coil has along the radiation region of the lamp module, is specified by means of the pitch of the coil. Together with the throughflow rate, all of these parameters determine the dwell time in the radiation region, which influences the yield or the reaction conversion, respectively. In an advantageous embodiment, the tube coil can be divided into coil segments and the latter can be connected to one another, in order to provide for a simpler handling and maintenance. A tube coil with variable coil diameters, which can simply be assembled from coil segments with different coil diameters, can thereby be advantageous in the case of variable process properties (e.g., viscosity, transmission) of the reactant fluid during the passage of the tube coil for the precise adaptation to the respective process.

According to a further embodiment of the helical photoreactor, the carrier device can further have at least one holding element, which is formed for holding a section of the tube coil, which can be present, e.g., on one of the tube windings, on the input section and/or on the output section. This means that the carrier device can also have several holding elements, which can differ, in order to be able to hold different tube coil sections. Such a holding element can thereby be formed in one piece with the engagement element or can be releasably or non-releasably connected to the engagement element. If the carrier device has more than one elongated guide element, for example two or preferably three guide elements, it is possible that a holding element engages only with one or with several of the guide elements or each guide element via one or several engagement element(s).

According to a further embodiment, the receiving space in the case of a helical photoreactor can further be sealed in a fluid-tight manner and the protective housing can have a housing inlet connection and a housing outlet connection for a first temperature control medium, which is transparent for the operating radiation of the lamp module. In this way, the receiving space, in which the lamp module and the carrier device with the tube coil are arranged, can be filled with the first temperature control medium, which is preferably a temperature control medium, which is liquid in the operating temperature range. The operating temperature range refers to a temperature range around a predetermined reaction temperature, which sets in the tube coil for performing the photochemical reaction or which is set by means of the temperature control medium. In most cases, the temperature control medium can be a cooling medium, in order to keep a predetermined reaction temperature approximately constant, e.g., in response to an exothermal reaction. The first temperature control medium further serves the purpose of preventing a heat transmission to the lamp module. In an advantageous embodiment, the temperature control medium can be circulated through the housing inlet connection and the housing outlet connection, in order to dissipate received heat outside of the protective housing.

A liquid, which is transparent for the entire emission spectrum of the lamp module or only for a range, which comprises the operating radiation, can be selected as temperature control medium. Filter liquids or filter compositions, which act as cut-off filter (absorption of short-wave radiation below a certain wavelength) or bandwidth filters, which are transparent only for radiation within a certain wavelength range, which comprises the operating radiation, can thus also be used as temperature control medium. Alternatively, to a filter liquid or liquid filter composition, the material of the tube coil or a filter coating applied thereto can provide a corresponding filter function.

A further embodiment of the helical photoreactor provides that the protective housing has a cylindrical receiving section, which is sealingly connected to a head plate on one end, to which the at least one lamp module is releasably fastened. On the other end, the cylindrical receiving section is sealingly connected either to a housing bottom or to a bottom plate. The terms with "head" and "bottom" refer to a vertical alignment of the protective housing or of the helical photoreactor, respectively, so that the head plate represents the upper boundary of the protective housing, and the housing bottom or the bottom plate, respectively, the lower boundary of the protective housing. However, a vertical alignment of the helical photoreactor is not mandatory for the operation, so that the helical photoreactor can also be operated in horizontal alignment. The terms "head" and "bottom" thus predominantly serve the purpose of differentiating the two ends and are not to limit a spatial orientation of the helical photoreactor. It is to further be understood that the cylindrical receiving section is to not be limited to a circular cylindrical shape but, deviating therefrom, can also be a cylinder with an elliptical or oval or an angular or rounded polygonal cross section.

According to a further embodiment of the helical photoreactor, the housing inlet connection for the first temperature control medium is arranged on the housing bottom or adjacent to the bottom plate on the cylindrical receiving section. The housing outlet connection for the first temperature control medium is located adjacent to the head plate on the cylindrical receiving section, so that the first temperature control medium flows as completely as possible through the receiving space, i.e., without short circuit flows. For this purpose, housing inlet and housing outlet connection can further be arranged diametrically offset on the protective housing.

According to yet a further embodiment of the helical photoreactor, it can be provided that the input section and the output section of the tube coil are present on the same side and extend in particular in a direction parallel to a longitudinal axis of the tube coil. The axis of rotation of an imaginary rotational body, such as, for example, of a circular cylinder, is defined as longitudinal axis of the tube coil, around the jacket of which the windings are wound. The input section and the output section can extend out of the protective housing either through the head plate or through the bottom plate in this way. The head plate or bottom plate, respectively, have corresponding sealed openings for the passage of the input and output section. The arrangement of the input and output section of the tube coil in the bottom plate can be particularly advantageous when the lamp module is fastened to the head plate, so that the assembly and the connection of tube coil and lamp module can take place from different sides of the protective housing. So that the input section and the output section of the tube coil are present on the same side, the tube coil can be formed as double-threaded tube coil, in the case of which first windings of a first winding pitch connect to the input section all the way to a return winding, from which second windings of a second winding pitch extend all the way to the output section. The thread pitch is thereby selected so that the second windings run between the first windings. Alternatively to a double-threaded tube coil, it can be provided for the arrangement of the input and output section on the same side that a return line extends from one end of the windings next to the windings to an output section, which is thus located on the same side as the input section, which connects directly to the other end of the windings. To avoid a shading of the windings in the radiation region of the lamp module, the return line can preferably run outside of the windings.

According to a further embodiment of the helical photoreactor, the lamp module has immersion tube and at least one lamp, which is arranged in the immersion tube. The lamp module has a immersion tube inlet connection and a immersion tube outlet connection, which communicate with a immersion tube interior space, which is limited by the immersion tube, so that the immersion tube interior space can be filled or flown through, respectively, with a second temperature control medium. The second temperature control medium is preferably a liquid cooling medium, in order to dissipate heat from the lamp in order to protect against overheating and to extend the service life. If an electrically non-conductive liquid is used as liquid cooling medium, a cladding tube in addition to the immersion tube around the lamp can be forgone thereby. The electrically non-conductive cooling medium can thus be brought directly into contact with the lamp surface for a more effective heat transmission. In an advantageous embodiment, the cooling medium is circulated through the immersion tube inlet connection and the immersion tube outlet connection, in order to dissipate absorbed heat outside of the protective housing. Immersion tube as well as cooling medium are transparent at least for the operating radiation. This means that the material of the immersion tube can be transparent for the entire emission spectrum of the lamp module or only for a range, which comprises the operating radiation. The liquid selected as cooling medium can likewise be transparent for the entire emission spectrum of the lamp module or only for a range, which comprises the operating radiation. It is further possible that instead of the first temperature control medium, the immersion tube and/or the cooling medium can have a filter function, in order to absorb, for example, short-wave radiation below a certain wavelength or to be transparent only for radiation within a certain wavelength range, which comprises the operating radiation.

According to a further embodiment, the lamp module of a helical photoreactor can further have a head part comprising at least one electrical connecting element, which is connected to an electrical connecting element of the lamp. The head part is arranged on the head plate, wherein the immersion tube inlet connection and the immersion tube outlet connection extend through the head part and/or through the head plate. Head plate and head part can be separate components, which are connected to one another, but it is also conceivable that the head plate can be formed as integral part of the head part. The head part or the head plate or both are formed to keep the lamp and/or the immersion tube sealed. It is comprised thereby that the head part is arranged on the immersion tube for sealing the immersion tube interior space, while the immersion tube is sealingly held by the head plate for positioning the lamp module in the protective housing.

The lamp used in the lamp module of a helical photoreactor can generally be any radiation source, which emits the desired operating radiation. Known UV radiation sources are, for example, medium- and low-pressure mercury vapor lamps. According to a further embodiment of the helical photoreactor, an LED lamp can preferably be used due to its comparatively low power consumption, long service life and the high switching capacity in the case of spontaneously full luminous flux. The LED lamp has a plurality of light-emitting semiconductor components (LEDs), which are arranged on a carrier body so as to be distributed over the jacket surface thereof. The carrier body can preferably be made as cooling body of a heat-conducting material, such as, e.g., aluminum. A fluid duct, which is connected to the immersion tube inlet connection on a head-side end of the carrier body, extends through the carrier body. On the other, bottom-side end of the carrier body, the fluid duct leads through an inlet opening into the immersion tube interior space, which is in fluidic connection with the immersion tube outlet connection via an outlet opening, which is present adjacent to the head-side end of the carrier body in the head part or the head plate, respectively. Electrically non-conductive cooling medium supplied via the immersion tube inlet connection can thus escape into the immersion tube interior space on the bottom-side end of the carrier body, flow along the jacket surface of the carrier body with the LEDs to the head-side end and can be discharged through the immersion tube outlet connection via the outlet opening.

In this way, the electrically non-conductive liquid cooling medium can absorb heat, which is generated by the LEDs and which is dissipated via the carrier body, not only in response to passing through the fluid duct, but also absorbs heat by means of the direct contact with the LEDs when flowing through the immersion tube interior space. Due to this effective heat dissipation, temperature peaks are avoided, which do in fact develop as a function of the arrangement and the performance of the LEDs during operation and which can lead to the shortening of the service life of the LEDs. In the case of nominal power, the LEDs can thus be operated with high currents, in order to reach a high light yield or radiation intensity, respectively, which is necessary for chemical syntheses in photoreactors. In addition to the improved cooling of the LEDs, the liquid cooling medium additionally advantageously provides an increased total light or radiant power, respectively, because the photon decoupling efficiency at the phase boundary diode surface-immersion tube interior space is increased due to the refractive index of the liquid cooling medium, and the reflection at the phase boundary immersion tube interior space-immersion tube wall is decreased.

According to yet a further embodiment of the helical photoreactor, it can be provided that the cooling medium used in the cooling body differs from the non-conductive cooling medium in the immersion tube, wherein the fluid duct in the cooling body does not lead into the immersion tube interior space, but extends through the cooling body, and has a separate inlet and outlet connection on the head-side end of the carrier body. The cooling of the cooling body can then take place with a conventional cooling medium, such as water, ethylene glycol or other cooling media, while the immersion tube is filled with the above-described non-conductive liquid, which remains stationary or the temperature of which is controlled by means of a separate cooling circuit, respectively, the immersion tube inlet connection and immersion tube outlet connection of which differ from the separate inlet and outlet connection of the cooling body. The cooling of the lamp is thus separated from the thermal decoupling to the process.

Lastly, a further embodiment of the helical photoreactor provides that the protective housing is pivotably mounted about a pivot axis, which runs at a right angle to a longitudinal axis of the protective housing or of the tube coil, respectively, with the lamp module. In this way, the protective housing can be pivoted with the carrier device located therein, which carries the one or optionally several tube coil(s), and the lamp module, so that the protective housing can be transferred from a vertical arrangement into a horizontal arrangement, and obviously also vice versa from horizontal into vertical. For this purpose, the helical photoreactor can have corresponding frame or holding constructions, respectively, comprising articulated connections as pivoting device. The helical photoreactor can thus, for example, be operated in the vertical arrangement, and assembly, replacement and maintenance operations can be performed in the horizontal arrangement, or vice versa. The pivoting device is to thereby not be limited to a pivot range of 90° between a single vertical arrangement and a horizontal arrangement of the protective housing, but it can also allow for other pivot angles, e.g., by pivoting about 180° or 360°. It is possible, for example, to quasi turn the helical photoreactor upside down by 180° for assembly, replacement and maintenance operations. It is thereby generally also conceivable that the helical photoreactor can be arranged in an orientation lying between the horizontal and vertical, if this is expedient for the operation or the maintenance.

Further embodiments as well as some of the advantages, which are associated with these and further embodiments, become clear and more easily understandable by means of the following in-depth description with reference to the accompanying figures. Objects or parts thereof, which are essentially identical or similar, can be provided with the same reference numerals. The figures are only a schematic illustration of an embodiment of the invention.

DETAILED DESCRIPTION

The device according to the disclosure is a photochemical helical photoreactor for the continuous production of a photochemical reaction product at the large or industrial scale, respectively, which can be scaled from the laboratory or pilot scale.

Figure 1:
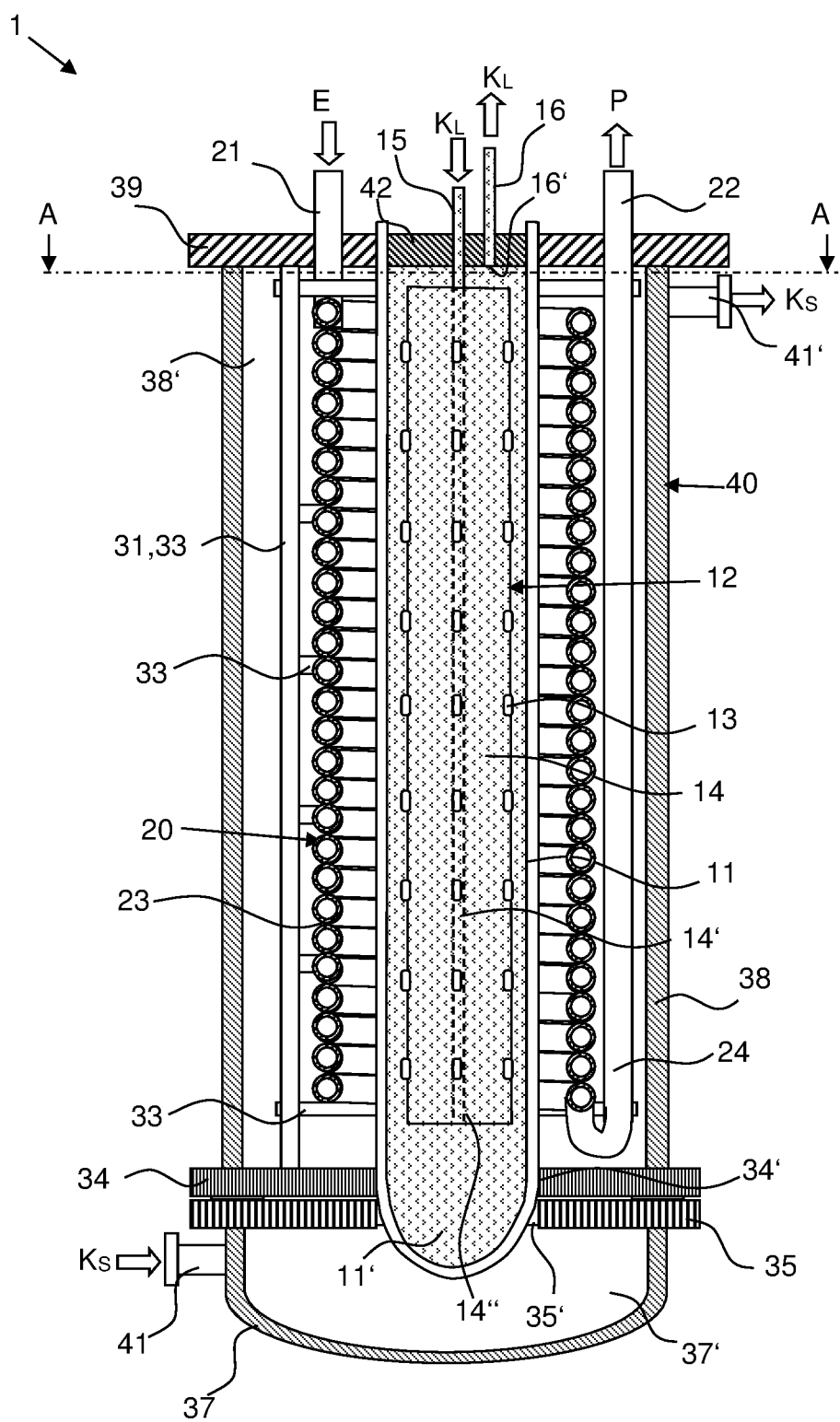
FIG. 1 shows a longitudinal sectional view of a photochemical helical photoreactor.
Figure 2:
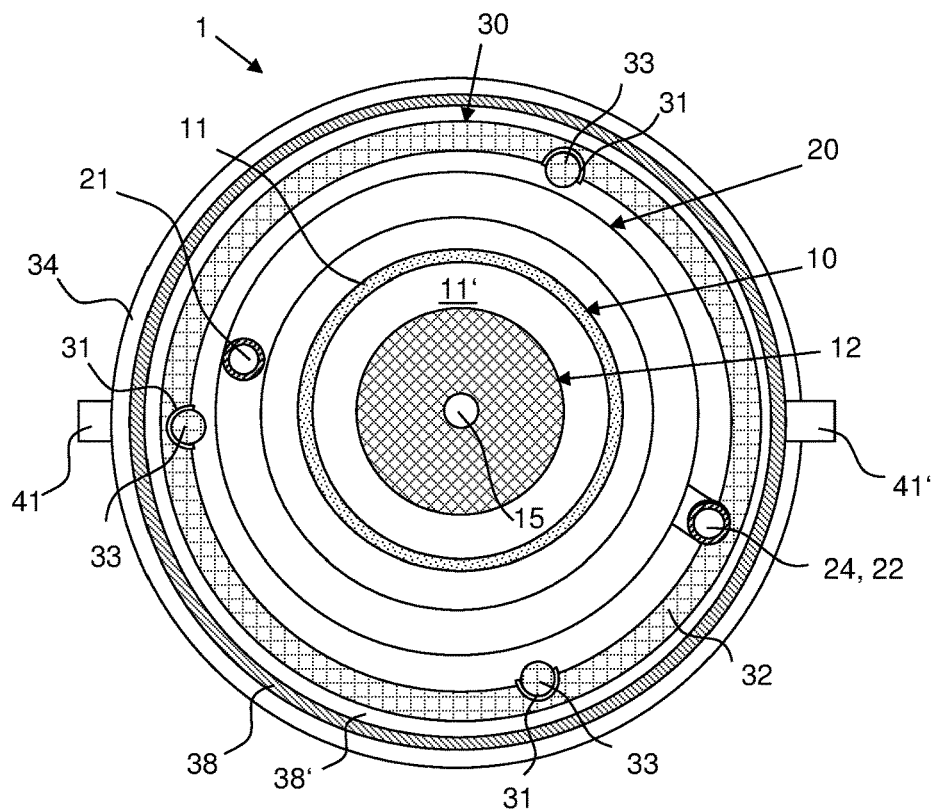
FIG. 2 shows a cross sectional view of the photochemical helical photoreactor from FIG. 1 along sectional line A-A.
Figure 3:
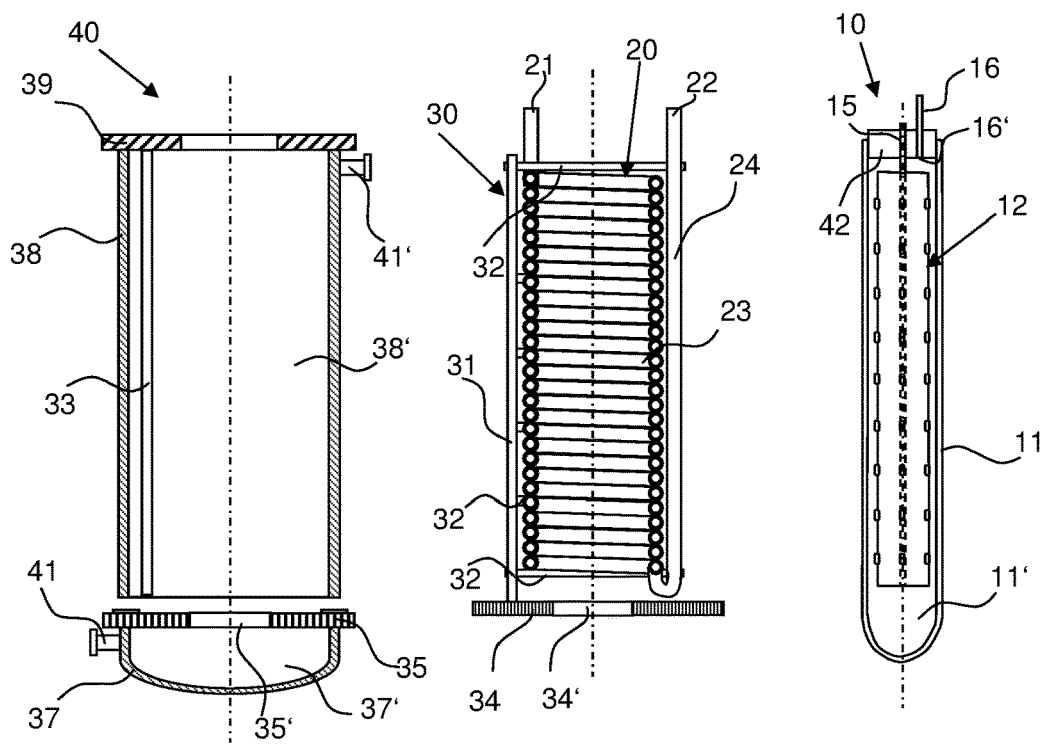
FIG. 3 shows a longitudinal sectional view of a disassembled photochemical helical photoreactor according to FIG. 1.
Figure 4:
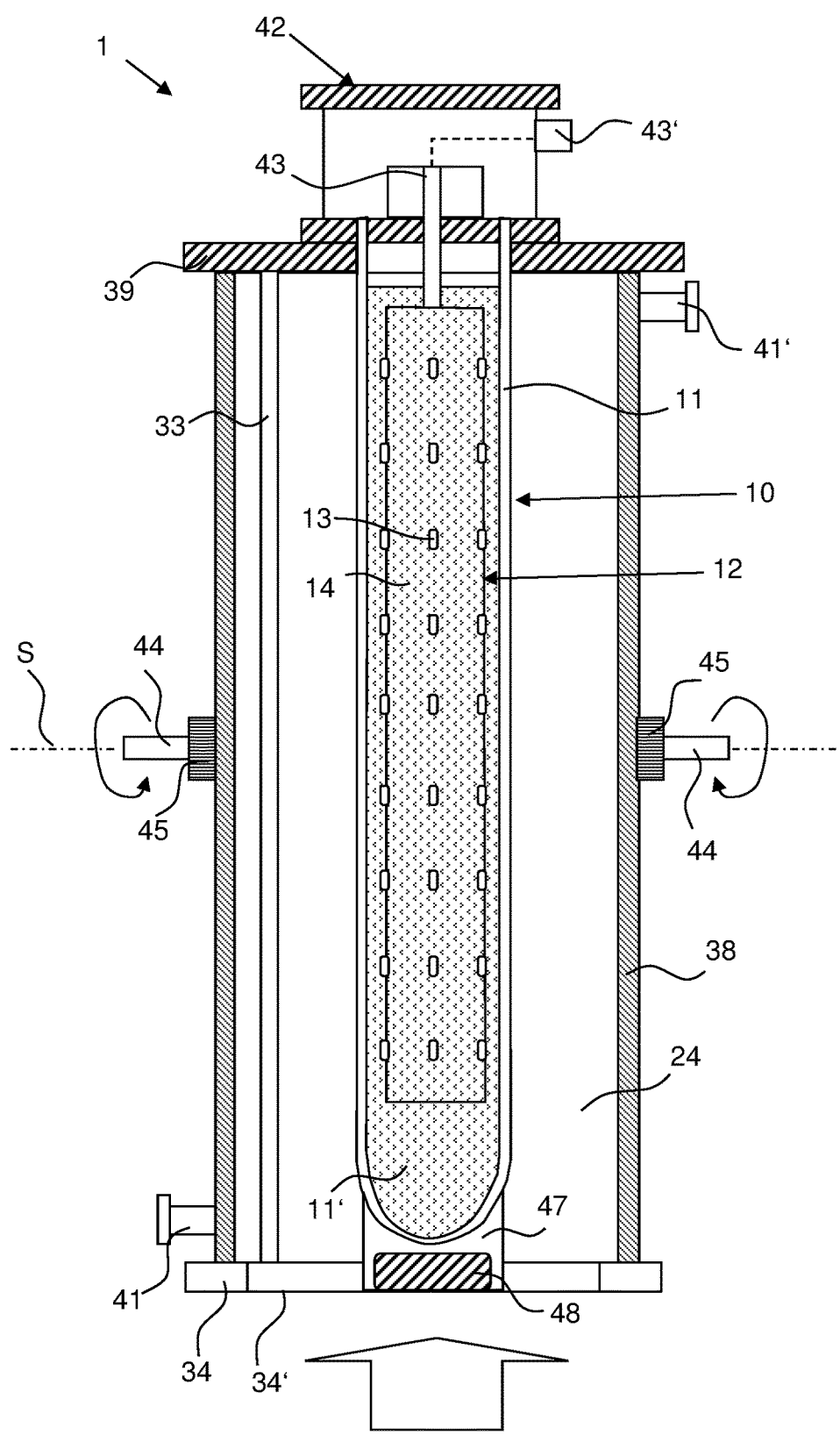
FIG. 4 shows a longitudinal sectional view of a photochemical helical photoreactor according to a further embodiment prior to final assembly.
Figure 5:
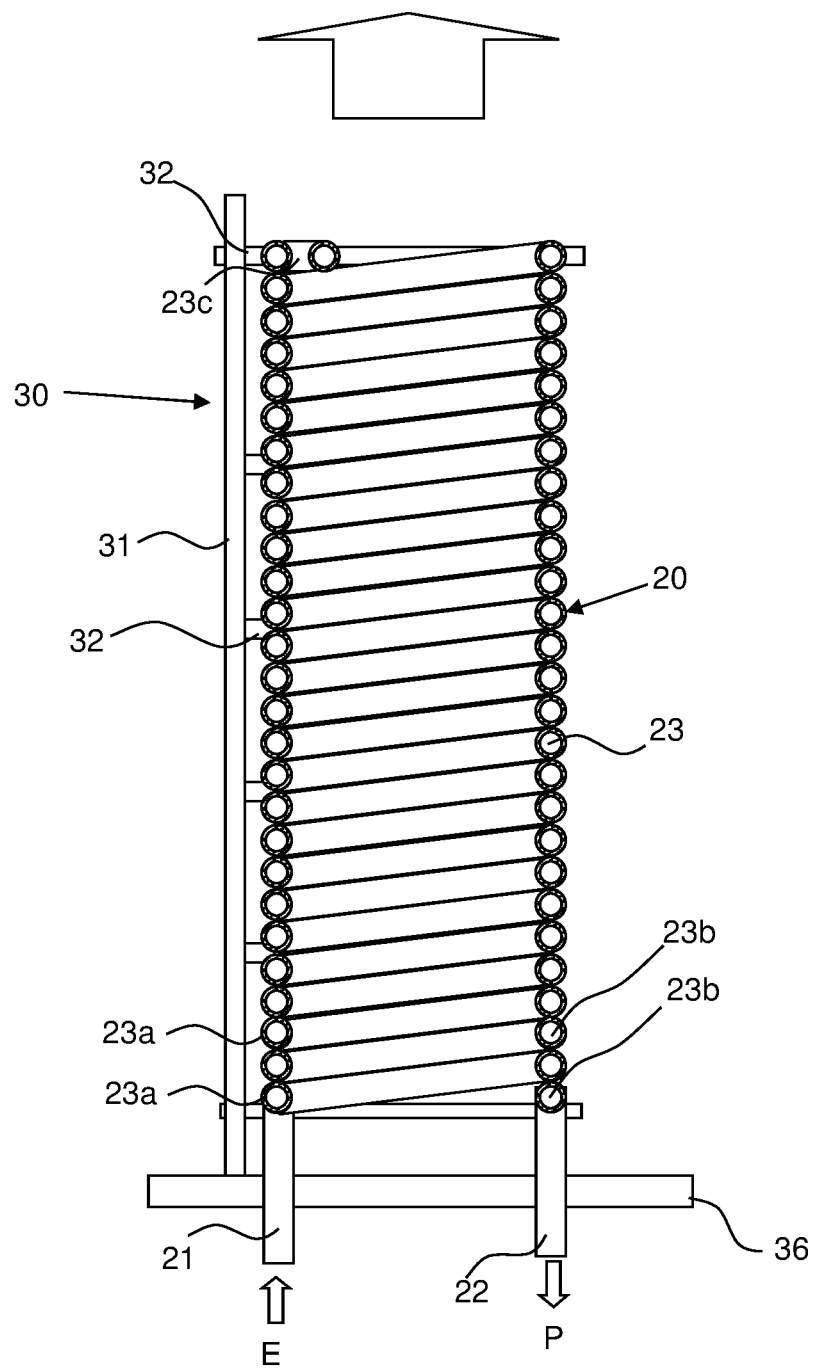
FIG. 5 shows a longitudinal sectional view of the carrier device of the photochemical helical photoreactor from FIG. 4.

The helical photoreactor 1 for the continuous production of a product fluid P from a reactant fluid E illustrated in FIGS. 1 and 2 has a lamp module 10, a tube coil 20, a carrier device 30 and a protective housing 40 as reactor components, which can also be seen in FIG. 3. FIGS. 4 and 5 show a further example of a helical photoreactor 1, which differs in several details from the helical photoreactor 1 from FIG. 1-3, but which also consists of a lamp module 10, a carrier device 30 comprising a tube coil 20 and a protective housing 40.

The protective housing 40 surrounds a receiving space 38', which is sealed in a pressure-tight manner, in which the lamp module 10 and the tube coil 20 held by the carrier device 30 are arranged. The protective housing 40 consists of a receiving section 38, which is circular cylindrical here, which is sealingly connected to a head plate 39 on one end (on the head-side), to which the lamp module 10 is releasably fastened. It goes without saying that designs of a receiving section, which deviate from the circular cylindrical shape, are also possible. On the other end (on the bottom side), the receiving section 38 is sealingly connected or can be sealingly connected, respectively, via a base flange 34 to a housing bottom 37 (FIG. 1-3), which has a bottom flange 35 for this purpose, or to a bottom plate 36 (FIG. 5), respectively, by means of a suitable seal.

It is noted that the terms "head" and "bottom" refer to a vertical arrangement of the protective housing 40 with the reactor components lamp module 10, tube coil 20 and carrier device 30 arranged therein, wherein the head plate 39 is located on the top and the housing bottom 37 or the bottom plate 36, respectively, on the bottom. This does not mean, however, that a vertical arrangement is absolutely required for the operation, but only that this can be a preferred, advantageous arrangement. A helical photoreactor 1 can likewise be operated in horizontal or other orientation of the protective housing 40 with the reactor components lamp module 10, tube coil 20 and carrier device 30 located therein, if this is desirable.

Figure 6:
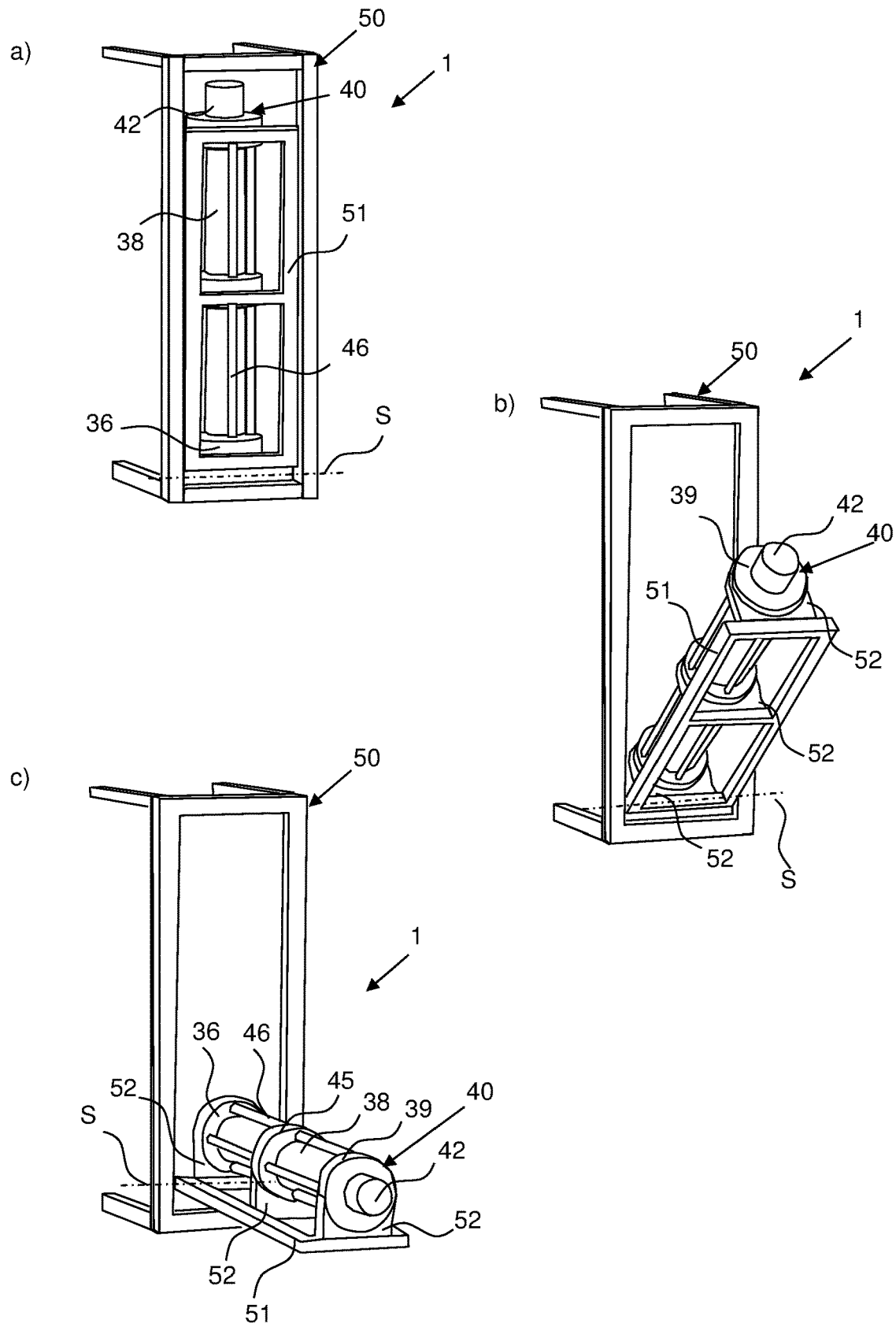
FIG. 6 shows three perspective views a-c of a photochemical helical photoreactor, which can be pivoted between a vertical arrangement a) and a horizontal arrangement c), according to a further embodiment.

As can be seen in the example of FIGS. 4 and 6, the helical photoreactor 1 can thereby have a pivot axis S, about which the protective housing 40 with the reactor components lamp module 10, tube coil 20 and carrier device 30 arranged therein can be pivoted between at least a vertical arrangement and at least a horizontal arrangement by 90° or 180°, respectively, optionally by 360°. The pivot axis S accordingly runs at a right angle to a longitudinal axis of the protective housing 40 or of the lamp module 10, respectively, or of the tube coil 20. The protective housing 40 with the reactor components lamp module 10, tube coil 20 and carrier device 30 arranged therein can thus be arranged in an orientation, which is desired for the operation and which can deviate from an alignment of the protective housing 40 for maintenance or assembly purposes, respectively. The example in FIG. 6 shows a helical photoreactor 1, the protective housing 40 of which with the reactor components lamp module, tube coil and carrier device arranged therein can be transferred from a vertical arrangement in FIG. 6a by pivoting about the pivot axis S (FIG. 6b) into a horizontal arrangement in FIG. 6c.

If the helical photoreactor 1 is operated, for example, in the vertical arrangement (FIG. 6a), the horizontal arrangement (FIG. 6c) can be used for assembly or maintenance purposes, respectively, in the case of which the protective housing 40 can be accessed well from the head side as well as from the bottom side, so that the carrier device with the tube coil and/or the lamp module can be removed and replaced easily. It goes without saying that deviating orientations of the protective housing 40 are conceivable for the operation and for the maintenance/assembly.

As can be seen in FIG. 6, the helical photoreactor 1 can comprise a rack 50, which surrounds the protective housing 40 in the vertical arrangement (FIG. 6a) in the illustrated example. The rack 50 is connected to a frame 51, which can be pivoted about the pivot axis S and to which the protective housing 40 is fastened. For this purpose, the frame 51 has three fastening sections 52 here, which are connected to the head plate 39, the bottom plate 36 and a fastening ring 45, which is arranged therebetween around the receiving section 38 and which is connected via fastening bars 46 to the head plate 39 and the bottom plate 36. In this example, the pivot axis S is located on the lower end of the frame 51, i.e., in the region of the bottom plate 36. It goes without saying that a pivoting device for pivoting the protective housing can be embodied differently than the rack 50 comprising frame 51, which is only illustrated in an exemplary manner. Instead of a rack, a container comprising closed walls can also be used, the arrangement of the pivot axis and fastening of the protective housing can vary.

Alternatively, to the example from FIG. 6, the pivot axis S, as illustrated in FIG. 4, can be provided in a central region of the protective housing 40, so that fewer acceleration forces develop in an advantageous manner when the protective housing 40 is pivoted with the components arranged therein. In the case of the arrangement of alignment elements 44 on the central fastening ring 45, a holding frame 51 can optionally be forgone and the protective housing 40 can be mounted directly in a corresponding rack or outer container, respectively, Both pivoting variations have advantages and disadvantages with regard to accessibility, space requirement and acceleration forces during the pivoting, but both ensure a simplification during the assembly/disassembly of lamp module and/or carrier device with tube coil into or out of the protective housing, respectively.

The tube coil 20 of the helical photoreactor 1 from FIG. 1-3 has a plurality of tube coils 23 and an input section 21 for supplying a reactant fluid E on the head-side end. The input section 21 extends parallel to the longitudinal axis of the tube coil 20, which corresponds to the axis of rotation of an imaginary circular cylinder, around the jacket of which the windings 23 are wound. On the bottom-side end, the tube windings 23 are connected to a return line 24, which extends on the outer side along the windings 23 parallel to the longitudinal axis all the way to an output section 22 for removal of the product fluid P with the reaction product. The output section 22 is thus arranged on the same side of the tube coil 20 as the input section 21 and parallel thereto, so that input and output section 21, 22 can be connected on the same side to a corresponding reactant and product line (not illustrated) in each case. The input section 21 as well as the output section 22 extend through the head plate 39 here. Corresponding openings for arranging the input section 21 and the output section 22 are provided there, which are sealed by means of suitable seals (not illustrated).

The tube coil 20 illustrated in FIG. 5 is embodied as double-threaded tube coil 20 with ascending windings 23a, which form a first winding pitch, and descending windings 23b, which form a second winding pitch, wherein the two winding pitches are connected on the head side by means of a return winding 23c. The input section 21, which is connected to the first ascending winding 23a, as well as the output section 22, which is connected to the last descending winding 23b, are thus located on the same side of the tube coil 20. Input and output section 21, 22 also run parallel to the longitudinal axis of the tube coil 20 here and run through the bottom plate 36 or openings provided therein, respectively, which are sealed accordingly, in this example.

Due to the fastening of the lamp module 10 to the head plate 39, the arrangement of the tube coil 20 with the input and output section 21, 22 on the bottom plate 36 is particularly advantageous because the connections of the tube coil 20 and the connections of the lamp module 10 are then located on opposite sides of the protective housing 40, and the assembly and disassembly is simplified. This arrangement of the input and output section 21, 22 of the tube coil 20 is thereby not limited to the double-threaded embodiment from FIG. 5 but can also be implemented accordingly for a tube coil 20 comprising return line 24, as in FIG. 1-3. Vice versa, a double-threaded tube coil without return section can also be used in a helical photoreactor 1 according to FIG. 1-3, in the case of which input and output section run through the head plate. Without pivotability, a corresponding assembly space would need to be kept free in each case above and below the protective housing 40 in the case of a vertically oriented protective housing 40, in order to provide for an assembly or disassembly, respectively, of the lamp module from the top and for an assembly or disassembly, respectively, of the carrier device with the tube coil from the bottom.

The pivotability can thereby be used expediently in that assembly or disassembly, respectively, only takes place from the top, even if only the carrier device 30 comprising the tube coil 20 is to be replaced. The protective housing 40 can then quasi be turned upside down in vertical orientation, so that the head plate 39, to which the lamp module 10 is fastened, points downwards, and the bottom plate 36, which is connected to the carrier device 30 and the tube coil 20, points upwards. With the bottom plate 36, the carrier device 30 with the tube coil 20 can then be removed upwards from the receiving space 38', while the lamp module 10 remains in the protective housing 40. After changing the tube coil 20 on the carrier device 30, it can be inserted again around the lamp module 10, before the helical photoreactor 1 is transferred into its operating arrangement after fastening the bottom plate 36 to the receiving section 38. The carrier device 30 can be firmly connected to the bottom plate 36 thereby, so that the insertion and removal of the carrier device 30 with the tube coil 20 takes place together with the bottom plate 36. Alternatively, the carrier device 30 with the tube coil 20 can be releasably connected to the bottom plate 36 when this appears to be more advantageous for weight reasons. During the assembly, the carrier device 30 with the tube coil 20 can then be inserted first, and the bottom plate 36 is then assembled or the bottom plate 36 is initially removed during the disassembly and the carrier device 30 with the tube coil 20 is then removed, respectively.

As can be seen in FIG. 1, the tube coil 20 surrounds the lamp module 10 in the helical photoreactor 1, wherein the tube coils 23 cover the radiation region of the lamp module 10. In FIG. 5, the tube coil 20 is formed with tube windings 23a, 23b, which cover the radiation region of the lamp module 10 when the tube coil 20 is arranged in the protective housing 40 around the lamp module 10, as suggested by the block arrow in FIG. 4. The supplied reactant fluid E is subjected to the operating radiation as reaction medium in response to the passage of the windings 23, 23a, 23b, whereby the photochemical reaction for the production of the reaction product is triggered, so that product fluid P is discharged from the tube coil. Different dwell times can be realized as a function of the pitch or number of the windings 23, 23a, 23b, respectively, the diameter of the windings and of the tube as well as the length of the wound tube section and the volume flow of the reactant fluid E. The diameter of the tube or of the windings, respectively, is selected on the basis of the hydrodynamic properties as well as of the absorption.

The tube windings 23, 23a, 23b are thus made of a material, which is transparent for the operating radiation of the lamp module 10, which can be a flexible plastic material or a rigid plastic or glass material. In the illustrated examples, the tube coils 20 are formed in one piece, so that the respective input and output sections 21, 22 or the return line 24, respectively, also consist of the same transparent material as the tube windings 23, 23a, 23b. Deviating therefrom, however, it can also be provided that the windings 23, 23a, 23b and the input and output sections 21, 22 or the return line 24, respectively, are manufactured separately and are connected to one another for forming a tube coil 20. In such a case, the input and output sections 21, 22 or the return line 24, respectively, can also consist of a different material, which is not transparent for the operating radiation, in order to ensure a good process control. To also ensure this in the case of one-piece tube coils 20, the return line 24 and optionally also the input and/or output section 21, 22 can be shaded. This can take place, e.g., by applying a coating, which absorbs the operating radiation, or by the arrangement of corresponding shielding elements.

The mechanical integrity of the tube coil can be problematic, depending on the material, so that the tube coil cannot be classified as pressure equipment under the PED (Pressure Equipment Directive) in accordance with AD 2000, optionally due to the material and due to aging, which may optionally be required for performing a photochemical reaction. In this case, the protective housing represents a safe containment system for protecting persons and the environment in the event of a leakage or the bursting of a tube coil made of plastic or glass.

A simple assembly and disassembly of the helical photoreactor 1 is made possible by means of a carrier device 30, which, as can be gathered from FIGS. 1 to 3 and 5, has various holding elements 32, which are releasably fastened to the windings 23, 23a, 23b, to the input and output sections 21, 22 or the return line 24, respectively. The holding elements 32 are connected with engagement elements 31, whereby the exemplary carrier device 30, as FIG. 2 shows, has three engagement elements 31 formed as elongated profile elements, which are arranged on an imaginary circular line around the tube coil 20 and extend parallel to the axis of rotation of the tube coil 20, which corresponds to the longitudinal axis of the lamp module 10 in the case of arrangement in the helical photoreactor 1. In order to ensure the correct positioning of the carrier device 30 with the tube coil 20 in the protective housing 40 with respect to the lamp module 10, the helical photoreactor 1 has, corresponding to the three elongated engagement elements 31, three elongated guide elements 33, which are present in the protective housing 40 parallel to a longitudinal axis defined by the lamp module 10. With the engagement elements 31, the carrier device 30 with the tube coil 20 can be inserted into the protective housing 40 in correct position with respect to the lamp module 10 on the elongated guide elements 33.

In the advantageous embodiment, which is shown in FIGS. 4 and 5 and which clarifies that the connection of the tube coil 20 takes place by means of the bottom plate 36, the rotational position of the tube coil 20 plays no role, so that the elongated guide elements 33 can be arranged in the protective housing 40, and the engagement elements 31 of the carrier device 30 so as to be distributed evenly on the imaginary circular line around the tube coil 20. In the event that the tube coil 20 can be assembled in the protective housing 40 only in a certain rotational position around the lamp module 10, so that, as in the example of FIGS. 1 to 3, the position of the input and output section 21, 22 of the tube coil 20 corresponds to the openings in the head plate 39 provided for this purpose, the arrangement of the elongated guide elements 33 in the protective housing 40 can deviate from a rotationally symmetrical arrangement. With corresponding asymmetrical arrangement of the engagement elements 31, the carrier device 30 can only be inserted in a single rotational position, in which the elongated guide elements 33 are aligned with the engagement elements 31.

The carrier device formed as rack in this way can receive different tube coils made of flexible or rigid plastic or of glass. The windings of a tube coil made of flexible plastic material can accordingly be wound onto the carrier device in different diameters and lengths, while tube coils made of rigid plastic or glass can be inserted into the carrier device. By means of the simple insertion and removal into the and out of the protective housing, fitting and replacement of the carrier device can be performed comfortably outside of the protective housing and independently of the lamp module. If the carrier device is fitted with the tube coil, the carrier device is inserted with the engagement elements into the protective housing on the elongated guide elements and is thereby automatically pushed over the lamp module, so that the windings of the tube coil are irradiated from the inside by means of the lamp module during operation of the helical photoreactor.

Modifications to the guide elements and the engagement elements, which deviate from the illustrated examples with respect to number and embodiment, are readily possible and fall under the scope of protection. A helical photoreactor can thus have more or fewer than three guide elements and three engagement elements, which can be present in different arrangement in the protective housing. Differently than shown, it is also possible that the holding elements are not connected to an elongated engagement element but that individual or all holding elements are formed with separate engagement elements, which can be engaged with one of the elongated guide elements in the protective housing. With respect to the elongated guide elements, it is further conceivable that they are not present as separate components, as illustrated, but can be formed, for example, on the inner wall of the protective housing. And alternatively to the illustrated rail guide, the elongated guide element can be formed, for example, similar to a guide spindle, on which, for example, slide bushing elements made of plastic, e.g., PTFE, can be guided as engagement elements of the carrier device.

The protective housing 40 sealed for the operation of the helical photoreactor 1 does not only serve as safety enclosure but also for controlling the temperature of the tube coil 20 or of the reaction medium guided therein, respectively, from the outside, in order to set an optimal temperature during the photochemical reaction. After closing the protective housing 40, the receiving space 38' is filled with a liquid temperature control medium $K_s$, which is transparent for the operating radiation of the lamp module 10. For this purpose, the protective housing 40 has a housing inlet connection 41, which, in the example of FIGS. 1 to 3, is arranged on the housing bottom 37 and, in the example of FIGS. 4 and 5, on the cylindrical receiving section 38 adjacent to the bottom plate 36. In order to circulate the temperature control medium $K_s$ for a better temperature control, the protective housing 40 further has a housing outlet connection 41', which is arranged adjacent to the head plate 39 on the cylindrical receiving section 38 and diametrically to the housing inlet connection 41. For the circulation, corresponding circulation lines (not illustrated), which are connected in the known way to a pump and optionally a heat exchanger, then connect to the housing inlet connection 41 and the housing outlet connection 41'.

Exemplary temperature control media $K_s$ comprise electrically non-conductive cooling liquids, such as, e.g., silicon oils, but also simple cooling liquids, such as water and ethylene glycol. Filter liquids can optionally further be used as temperature control medium $K_s$, in order to briefly absorb radiation of the lamp module below a certain wavelength as cut-off filter liquid or to only allow (UV) radiation of the lamp module within a certain wavelength range as bandwidth filter liquid. Aqueous compositions for filter solutions of this type are known from the prior art, whereby different filter wavelengths can be set by variation of the concentration and mixing of dissolved salts (e.g., $Cu-SO_4$, $Fe_2(SO_4)_3$, $FeSO_4$, $FeCl_3$, $Na_2WO_4$, $SnCl_2$, $Na_3VO_4$, $BiCl_3$, $KVO_3$, $KNO_2$, $K_2CrO_4$, $NiSO_4$, $CoSO_4$, ...).

The lamp module 10 illustrated in the helical photoreactor 1 in FIGS. 1 to 5 has a immersion tube 11, which is arranged coaxially in the tube coil 20. On the head-side end, the immersion tube 11, which is closed on the bottom side, is received by the head plate 39, so that a immersion tube interior space 11' enclosed by the immersion tube 11 is separated from the receiving space 38' in the protective housing 40, which is optionally filled with the temperature control medium $K_s$. The closed end of the immersion tube 11 is mounted in the bottom region of the protective housing 40, in order to hold the immersion tube 11 in a stable manner. For this purpose, corresponding coaxially formed passage openings 34', 35' can be seen in FIGS. 1 to 3 in the base flange 34 and the bottom flange 35, which, in contrast to the illustration, could have further passage openings, so that the temperature control medium $K_s$ supplied through the housing inlet connection 41 on the bottom section 37 can flow out of the bottom space 37' into the receiving space 38'. The lamp module 10, which is shown in FIG. 4, is mounted to the closed end of the immersion tube 11 in a holder 47, which is spring-loaded by means of spring element 48 and which comes to rest on the bottom plate 36 after insertion of the carrier device 30 with the tube coil 20 from FIG. 5 and the connection of the base plate 36 to the base flange 34.

A lamp 12, which emits the operating radiation and optionally also radiation with wavelengths, which deviate from the operating radiation, is arranged in the immersion tube 11. For the cooling of the lamp 12 and for the thermal decoupling from the receiving space 38', the lamp module 10 has a immersion tube inlet connection 15, via which the immersion tube interior space 11' can be filled with a further liquid temperature control medium $K_L$, which, like the immersion tube 11, is selected to be transparent at least for the operating radiation. For the circulation of the second temperature control medium $K_L$, the lamp module 10 further has a immersion tube outlet connection 16, by means of which the heated temperature control medium $K_L$, is discharged from the immersion tube interior space 11' via non-illustrated circulation lines and is supplied again via the immersion tube inlet connection 15 after dissipation of the absorbed heat outside of the protective housing 40.

For the connection of the cooling circuit and for the electrical connection of the lamp 12, the lamp module 10 has a head part 42, which sealingly closes the immersion tube 11 on the head-side end. The head part 42 from FIGS. 1 to 3 is not connected directly to the head plate 39, which may well be the case, however, as FIGS. 4 to 5 shows: the head part 42 is connected to the head plate 39 there. Deviating therefrom, head plate and head part can also be present so as to be integrated in a component (not illustrated). FIGS. 1 to 3 show that the immersion tube inlet connection 15 and the immersion tube outlet connection 16 extend through the head part 42 for the connection of the immersion tube interior 11' to a cooling circuit, while the head part 42 in FIG. 4 shows an electrical connecting element 43, which is connected to the lamp 12 and which is connected to a further electrical connecting element 43' for the connection to an external power source. The separate illustration of the coolant and power connections of the head parts 42 in FIGS. 1 to 3 and 4 thereby only serves for the better overview and does not represent any limitation whatsoever. On the contrary, it goes without saying that the lamp module 10 from FIGS. 1 to 3 also has corresponding electrical connecting elements for the power supply of the lamp 12, and the lamp module 10 from FIG. 4 can have corresponding immersion tube inlet and immersion tube outlet connections for a coolant $K_L$.

Control cabinets and control gear, which a helical photoreactor can comprise for controlling the lamp by means of power setting (optionally also by pulsing the lamp) and which can be formed, for example, for the secure switch-off according to the ATEX guidelines, are not illustrated.

As radiation source, the lamp modules 10 in the shown helical photoreactors 1 have an LED lamp 12 comprising several LEDs 13, which are arranged on a carrier body 14 so as to be distributed over the jacket surface thereof. Compared to conventional radiation sources, an LED lamp can preferably be used in the case of spontaneously full luminous flux, due to its comparatively low power consumption, long service life and the high switching capacity. The operating radiation of the LED lamp 13 can be set systematically by means of suitable selection of the LED 13 because the wavelength of the radiation emitted by LEDs is a function of the doping of the semiconductor component. Even though LEDs are not radiant heaters, high temperatures, which do in fact develop during the operation as a function of the arrangement and the performance of the LEDs, significantly shorten the service life of the LEDs. In order to operate the dimmable LEDs for a high light yield or radiation intensity, respectively, with high currents, an effective heat dissipation is required in order to maintain the service life of the LEDs.

For the heat dissipation, the carrier body 14 can thus consist of a metal, in particular aluminum. Due to the fact that this heat dissipation is often not sufficient when using photoreactors for chemical syntheses, which can run strongly exothermally, a fluid duct 14' extends through the carrier body 14, which simultaneously acts as cooling body, in order to at least partially transmit heat, which the carrier body 14 absorbed from the LEDs 13, to the cooling fluid $K_L$, which flows through the fluid duct 14' in the case of the illustrated LED lamp 12. For this purpose, the fluid duct 14' is connected on a head-side end of the carrier body 14 to the immersion tube inlet connection 15, which extends through the head part 42. In a non-illustrated variation, it is conceivable that the course of the fluid duct within the carrier body has a return on the bottom-side end, so that the fluid duct can also be connected to the immersion tube outlet connection on the head-side end of the carrier body.

It is shown figuratively that the fluid duct 14' leads to the bottom-side end of the carrier body 14 through an inlet opening 14" in the immersion tube interior space 11, so that the cooling fluid $K_L$, which is supplied on the head-side end through the immersion tube inlet connection 15, escapes on the bottom-side end of the carrier body 14 and flows along the surface of the LED lamp 12 to the head-side end of the lamp module 10, where it reaches through an outlet opening 16' on a side of the head part 42 facing the immersion tube interior space 11 into the immersion tube outlet connection 16, which extends parallel to the immersion tube inlet connection 15 through the head part 42. Connecting lines, which are connected to the immersion tube inlet and immersion tube outlet connection 15, 15 for forming a cooling circuit with pump and optionally heat exchanger, are not illustrated. Heat, which the cooling fluid $K_L$, has absorbed by means of the direct contact with the LEDs 13, can thus be dissipated outside of the lamp module 12. By circulating the cooling fluid $K_L$, the temperature control of the lamp 12 can take place independently of a temperature control of the reaction medium in the tube coil 20.

Due to the fact that the cooling fluid $K_L$, directly contacts the LEDs 13 and the electrical connections thereof and is located in the radiation region of the lamp 12, an electrically non-conductive, i.e., electrically insulating liquid, is selected as cooling fluid $K_L$, which is transparent for the operating radiation. With respect to the cooling of the LEDs 13 and the thermal decoupling from the receiving space 38', the lamp module 10 is thus improved and furthermore provides an increased total light or radiant power, respectively, i.e., an increased radiation quantity and density on the outer surface of the immersion tube, with respect to the lamps according to the prior art because, due to a refractive index, which is significantly larger than the refractive index of air or inert gas and which lies in the range of approximately 1.35 to approximately 1.55 (at 20° C.) in the case of suitable non-conductive liquids, the non-conductive liquid provides an increased photon decoupling efficiency on the phase boundary diode surface-immersion tube interior space and a decreased reflection on the phase boundary immersion tube interior space-immersion tube wall and thus avoids near field reflections.

It is further advantageous that an accelerated aging of the primary optics of the LEDs is avoided, which are present in particular in chemical plants, in which VOCs ("volatile organic compounds") are present, which can develop even when using an inert gas, such as nitrogen because VOCs penetrate into the primary optics, which are usually embodied as silicon lens, cloud the latter and thus lower the light yield. Due to the fact that the primary optics are shielded from VOCs by means of the non-conductive liquid, the aging process is significantly slowed down.

For example, low-viscosity silicon oils, which are transparent and non-flammable all the way into the medium UV-C range, can be used as liquid coolant $K_L$. Depending on the wavelength of the operating radiation, fluorinated hydrocarbons, such as perfluorocarbons and hydrofluoroethers can optionally also be used as coolant $K_L$, which are advantageously non-flammable, but have absorption bands within certain wavelength ranges: if the operating radiation lies outside of the absorption bands, fluorinated hydrocarbons, such as, for example, 3M fluorinated electronic liquid or 3M Novec high-tech liquid by 3M™ (3M electronics, St. Paul, USA) can be used.

Highly refined mineral oils can further be resorted to as coolant $K_L$, in particular within the spectral range of below 250 nm, which mainly comprise saturated hydrocarbons. Alkanes and cycloalkanes are advantageously transparent from the visible wavelength range all the way into the wide UV-C range and in the case of sufficiently low distance between LED and immersion tube of up to 195 nm. When using highly refined mineral oils as coolant, however, attention has to be paid to a careful and sealed exclusion of air, in order to avoid the formation of flammable steam-air mixtures. Further alternative examples for a coolant $K_L$, comprise synthetic ester and ether compounds. Compared to mineral oils, synthetic organic ester oils, which are transparent all the way into the medium UV-C range, have the advantage, for example, of a higher temperature resistance and higher burning and ignition temperature and are more environmentally friendly, but have a lower resistance to aging. In the case of ether compounds, such as, for example, 1,4-dioxane, the transmission all the way into the medium UV-range is also sufficient, but attention is to also be paid here to a careful exclusion of air during the construction of the lamp module, in order to avoid easily flammable steam-air mixtures.

Unless already mentioned, the temperature media $K_L$, listed for the lamp module 10 can also be selected as temperature control medium $K_s$ for cooling the tube coil 20. The same coolant as the temperature medium $K_L$, for cooling the lamp 12, can be used as temperature control medium $K_s$ for cooling the tube coil 20, or different temperature control media can be used. The two cooling circuits are preferably separated from one another, but both cooling circuits can optionally also be connected to one another, depending on developing temperature levels.

It goes without saying that further liquids can possibly also be used as coolant $K_L$, as long as they are electrically insulating and transparent for the wavelength of the operating radiation. In order to provide a transmission of at least 75%, which is required for the desired transparency, in particular at wavelengths of below 250 nm, the inner diameter of the immersion tube with respect to the outer diameter of the carrier body, which is fitted with the LEDs, can be selected so that the distance between the LED surface and the immersion tube inner wall, and thus the absorption by means of the coolant, is as small as possible. In the case of the design with respect to the distance between immersion tube and carrier body, it is to further be considered that the coolant is provided with a volume flow, which is sufficient for an optimal heat dissipation and suitable flow control.

Each helical photoreactor thus advantageously provides for a thermal decoupling and temperature control of the lamp, independently of the temperature control of the tube coil, i.e., of the reaction medium or product fluid, respectively, with the reaction product. It is thus possible to not only perform strongly exothermic reactions with large heat development, but, for example, also low temperature reactions without the formation of condensed water in the immersion tube. The helical photoreactor can further be flexibly adapted by means of the carrier device. The carrier device allows for the use of different tube coils, which can have different diameters, which are adapted to the spectral absorption and hydrodynamics (plug-flow) and/or different lengths for adapting the dwell time in correlation with the pressure loss as a function of the viscosity of the reaction or product medium, respectively. Tube coils, which can be used with the carrier device, can further differ with regard to the materials, which can have transmission values and pressure resistances, which are adapted depending on the reaction conditions. Tube coils made of solid plastic and glass materials also provide for smaller bending radii than can be achieved by forming a flexible plastic hose. Functionalized tube coils comprising immobilized catalysts can moreover be used, which can be fixed, for example, in a sol-gel process. For this purpose, a catalyst-containing coating solution (sol) can be applied to the inner surface, in order to reach the desired coating as gel film with preferably homogenous, amorphous structure and even, thin layer thickness, if possible without defects, after drying, in order to avoid radiation losses due to reflection or scattering, respectively, on the boundary surfaces. Tube coils made of quartz glass can be provided, for example, with an inorganic gel film based on $SiO_2$, which remains amorphous even after a solidification treatment at temperatures of above 400° C. The coating solution thereby contains at least a photocatalytic material and optionally further metal oxides (e.g., aluminum, titanium or yttrium oxide, . . . ), which can influence the optical properties of the tube coil surface, but which can optionally also act photocatalytically.

The separate arrangement of lamp module on one side and carrier device comprising tube coil on the other side in the protective housing further also provides for a simple replacement of the entire lamp module, in order to operate with operating radiations of different wavelengths. If the immersion tube is transparent in all wavelengths of the operating radiations, it is possible to leave the immersion tube in the protective housing and to only replace the lamp, in order to provide the desired operating radiation.

In contrast to conventional chemical photoreactors, which are mostly equipped for a batch operation with immersion lamps, the operational safety of the continuously operated helical photoreactor is increased because only comparatively small quantities of the reaction medium are located in the tube coil within the protective housing, which is designed as pressure container according to pressure equipment directives. The helical photoreactor, which allows for a simplified scaling from laboratory to industrial scale, is further not only suitable for performing photochemical reactions in the liquid phase, during which a liquid reactant fluid is supplied into the tube coil, the windings of which passes as liquid reaction medium and leaves the tube coil as liquid product fluid with the reaction product, but also for performing photochemical reactions in the gas phase.

The illustrated examples refer to a helical photoreactor, which has a tube coil, which is arranged around a lamp module and which is held by a carrier device, which, together, are arranged in a protective housing. The longitudinal axis of the lamp module is thereby identical with the longitudinal axis of the tube coil. In a non-illustrated modification, a helical photoreactor can also have several tube coils, which each surround a lamp module and are arranged in parallel in a protective housing, wherein a separate carrier device for each tube coil or a common carrier device for all tube coils can be provided. Modifications are likewise conceivable, in the case of which a helical photoreactor has two (or more) tube coils, which are arranged around a lamp module, wherein the windings of the tube coils have the same pitch and can be arranged offset according to a double-(or multi-) threaded thread. Two or more lamp modules can further be arranged parallel to the longitudinal axis of a tube coil next to one another or one behind the other along the longitudinal axis in a tube coil, in order to increase the radiant power or to realize different photochemical reactions by means of different wavelengths of the operating radiation. In a further embodiment, a helical photoreactor can further have additional lamp modules, which are arranged in the protective housing outside of the tube coil, so that the tube coil cannot only be irradiated from the inside, but also from the outside. A correct positioning of the tube coil with respect to the additional lamp module is also secured here by means of the carrier device.

LIST OF REFERENCE NUMERALS 1 helical photoreactor
10 lamp module
11, 11' immersion tube, immersion tube interior space
12 LED module
13 LED
14, 14', 14" carrier/cooling body, fluid duct, inlet opening
15 immersion tube inlet connection
16, 16' immersion tube outlet connection, outlet opening
20 tube coil
21 input section
22 output section
23, 23a, 23b tube winding
24 return line
30 carrier device
31 guided engagement element
32 holding element
33 elongated guide element
34, 34' base flange, passage opening
35, 35' bottom flange, passage opening
36 base plate
37, 37' protective housing bottom section, bottom space
38, 38' protective housing receiving section, receiving space
39 head plate
40 protective housing
41, 41' housing inlet connection, housing outlet connection
42 head part
43, 43' connecting element
44 alignment element
45 fastening ring
46 fastening bar
47 holder
48 spring element
50 rack
51 frame
52 fastening section
$K_L$ temperature control or coolant, respectively (lamp module)
$K_s$ temperature control or coolant, respectively (protective housing)
E reactant fluid
P product fluid
S pivot axis

The invention claimed is:

1. A helical photoreactor (1), comprising:
at least one lamp module (10);
at least one tube coil (20), which has a plurality of tube windings (23, 23a, 23b) between an input section (21) and an output section (22), the at least one tube coil (20) being arranged around the at least one lamp module (10);
a carrier device (30), which carries the at least one tube coil (20);
a protective housing (40),
wherein the protective housing (40) surrounds a receiving space (38'),
wherein the carrier device (30) with the at least one tube coil (20) and the at least one lamp module (10) are arranged in the receiving space (38'), and
wherein the carrier device (30) provides a predetermined positioning of the at least one tube coil (20) with respect to the at least one lamp module (10) and the protective housing (40); and
at least one elongated guide element (33), which is present in the protective housing (40) parallel to a longitudinal axis, the longitudinal axis being defined by the at least one lamp module (10),
wherein the carrier device (30) has at least one engagement element (31),
wherein the at least one engagement element (31) is arranged on the at least one elongated guide element (33) so as to be capable of being guided in a longitudinally movable manner and so as to be capable of being positioned,
wherein the at least one elongated guide element (33) specifies a positioning of the carrier device (40) with the at least one tube coil (20) by the at least one engagement element (31) guided on the at least one elongated guide element (33).

2. The helical photoreactor (1) according to claim 1,
wherein the carrier device (30) has at least one holding element (32), which is formed for holding at least one section of the at least one tube coil (20),
wherein the at least one holding element (32) and the at least one engagement element (31) are formed in one piece, or
wherein the at least one holding element is releasably or non-releasably connected to the at least one engagement element (31).

3. The helical photoreactor (1) according to claim 1,
wherein the receiving space (38') is sealed and
wherein the protective housing (40) has a housing inlet connection (41) and a housing outlet connection (41'), so that the receiving space (38') can be filled with a liquid temperature control medium ($K_5$).

4. The helical photoreactor (1) according to claim 3,
wherein the protective housing (40) has a cylindrical receiving section (38),
wherein the cylindrical receiving section (38) is fastened on one end to a head plate (39), to which the at least one lamp module (10) is fastened, and
wherein the cylindrical receiving section (38) is connected on another end to a housing bottom (37) or to a bottom plate (36).

5. The helical photoreactor (1) according to claim 4,
wherein the housing inlet connection (41) is arranged on the housing bottom (37) or adjacent to the bottom plate (36) on the cylindrical receiving section (38), and
wherein the housing outlet connection (41') is arranged adjacent to the head plate (39) on the cylindrical receiving section (38).

6. The helical photoreactor (1) according to claim 4,
wherein the input section (21) and the output section (22) are present on a same side of the at least one tube coil (20), and
wherein either
the at least one tube coil (20) is formed as a double-threaded tube coil (20) with
first windings (23a) of a first winding pitch that connect to the input section (21) and extend to a return winding (23c), and
second windings (23b) of a second winding pitch that extend from the return winding (23c) to the output section (22), or
a return line (24) is arranged between an end of the tube windings (23) facing away from the input section (21) and the output section (22).

7. The helical photoreactor (1) according to claim 5,
wherein the at least one lamp module (10) has an immersion tube (11) and at least one lamp (12), which is arranged in the immersion tube (11),
wherein the at least one lamp module (10) has an immersion tube inlet connection (15) and an immersion tube outlet connection (16), which communicate with an immersion tube interior space (11') limited by the immersion tube (11), so that the immersion tube interior space (11') can be filled with a second liquid cooling medium ($K_L$).

8. The helical photoreactor (1) according to claim 7,
wherein the at least one lamp module (10) has a head part (42) comprising at least one electrical connecting element (43'), which is connected to an electrical connecting element (43) of the at least one lamp (12),
wherein the head part (42) and/or the head plate (39), on which the head part (42) is arranged, is/are formed for sealingly holding the at least one lamp (12) and/or the immersion tube (11),
wherein the immersion tube inlet connection (15) and the immersion tube outlet connection (16) extend through the head part (42) and/or the head plate (39).

9. The helical photoreactor (1) according to claim 7,
wherein the at least one lamp (12) is an LED lamp (12),
wherein the LED lamp (12) has a plurality of LEDs (13),
wherein the LEDs (13) are arranged on a carrier body (14) so as to be distributed over a jacket surface thereof,
wherein a fluid duct (14') extends through the carrier body (14),
wherein the fluid duct (14') is connected on a head-side end to the immersion tube inlet connection (15) and, on a bottom-side end of the carrier body (14), leads through an inlet opening (14") into the immersion tube interior space (11'),
wherein the immersion tube interior space (11') communicates with the immersion tube outlet connection (16) via an outlet opening (16'), and
wherein the outlet opening (16') is present adjacent to the head-side end of the carrier body (14).

10. The helical photoreactor (1) according to claim 1,
wherein the helical photoreactor (1) has frame and/or holding constructions comprising articulated connections as a pivoting device,
wherein the protective housing (40) is pivotably mounted about a pivot axis(S),
wherein the pivot axis(S) runs at a right angle to a longitudinal axis of the protective housing (40), so that the protective housing (40) can be transferred from a vertical arrangement into a horizontal arrangement with the carrier device (30), and
wherein the carrier device (30) carries the at least one tube coil (20), and the at least one lamp module (10).

* * * * *